(12) United States Patent
Rekaya et al.

(10) Patent No.: US 10,569,026 B2
(45) Date of Patent: Feb. 25, 2020

(54) RESETTABLE DRUG DELIVERY DEVICE

(71) Applicant: Sanofi, Paris (FR)

(72) Inventors: Naceur Rekaya, Guildford (GB); Paul Richard Draper, Evesham (GB)

(73) Assignee: Sanofi, Paris (FR)

( * ) Notice: Subject to any disclaimer, the term of this patent is extended or adjusted under 35 U.S.C. 154(b) by 144 days.

(21) Appl. No.: 15/517,822

(22) PCT Filed: Oct. 9, 2015

(86) PCT No.: PCT/EP2015/073437
§ 371 (c)(1),
(2) Date: Apr. 7, 2017

(87) PCT Pub. No.: WO2016/055631
PCT Pub. Date: Apr. 14, 2016

(65) Prior Publication Data
US 2018/0071460 A1 Mar. 15, 2018

(30) Foreign Application Priority Data

Oct. 9, 2014 (EP) ..................................... 14306596

(51) Int. Cl.
*A61M 5/315* (2006.01)
*A61M 5/24* (2006.01)
*A61M 5/31* (2006.01)

(52) U.S. Cl.
CPC .......... *A61M 5/31543* (2013.01); *A61M 5/24* (2013.01); *A61M 5/3158* (2013.01);
(Continued)

(58) Field of Classification Search
CPC .......... A61M 5/31543; A61M 5/31533; A61M 5/31535; A61M 5/31536; A61M 5/31538;
(Continued)

(56) References Cited

U.S. PATENT DOCUMENTS

2015/0018771 A1* 1/2015 Schenker ................ A61M 5/20
604/189

FOREIGN PATENT DOCUMENTS

| EP | 2 274 030 | 9/2012 |
| EP | 2 644 218 | 10/2013 |

(Continued)

OTHER PUBLICATIONS

International Preliminary Report on Patentability in International Application No. PCT/EP2015/073437, dated Apr. 11, 2017, 6 pages.
International Search Report and Written Opinion in International Application No. PCT/EP2015/073437, dated Nov. 23, 2015, 10 pages.

*Primary Examiner* — Kami A Bosworth
*Assistant Examiner* — Leah J Swanson
(74) *Attorney, Agent, or Firm* — Fish & Richardson P.C.

(57) ABSTRACT

The present disclosure is generally directed to a resettable drug delivery device for selecting and dispensing a number of user variable doses of a medicament. The drug delivery device comprises a housing, a cartridge holder releasably attached to the distal end of the housing, a piston rod engaging a housing insert and a drive member, a dose setting member guided within the housing to allow rotation of the dose setting member during dose setting and dose dispensing, a clutch for rotationally coupling the drive member and the dose setting member, and a locking element which is rotationally constrained to the housing and is axially movable relative to the housing between a proximal dose setting position and a distal resetting position.

18 Claims, 3 Drawing Sheets
Specification includes a Sequence Listing.

(52) U.S. Cl.
CPC .... *A61M 5/31536* (2013.01); *A61M 5/31541* (2013.01); *A61M 5/31551* (2013.01); *A61M 5/31561* (2013.01); *A61M 2005/2485* (2013.01); *A61M 2005/3126* (2013.01); *A61M 2005/3154* (2013.01); *A61M 2205/581* (2013.01); *A61M 2205/582* (2013.01); *A61M 2205/584* (2013.01)

(58) Field of Classification Search
CPC .......... A61M 5/31541; A61M 5/31545; A61M 5/31548; A61M 5/3155; A61M 5/31551; A61M 5/31553; A61M 5/31556; A61M 5/3156; A61M 5/31561; A61M 5/31563; A61M 2005/3154
See application file for complete search history.

(56) References Cited

FOREIGN PATENT DOCUMENTS

| | | |
|---|---|---|
| JP | 2012-500067 | 1/2012 |
| WO | WO 01/72361 | 10/2001 |
| WO | WO 2009/132781 | 11/2009 |
| WO | WO 2011/154486 | 12/2011 |
| WO | WO 2012/049143 | 4/2012 |
| WO | WO 2012/152666 | 11/2012 |
| WO | WO 2013/144021 | 10/2013 |
| WO | WO 2014/033195 | 3/2014 |

* cited by examiner

RESETTABLE DRUG DELIVERY DEVICE

CROSS-REFERENCE TO RELATED APPLICATIONS

This application is a U.S. national stage application under 35 USC § 371 of International Application No. PCT/EP2015/073437, filed on Oct. 9, 2015, which claims priority to European Patent Application No. 14306596.9 filed on Oct. 9, 2014, the entire contents of which are incorporated herein by reference.

TECHNICAL FIELD

The present disclosure is generally directed to a drug delivery device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

Manually driven reusable drug delivery devices are known e.g. from WO 2014/033195 A1 and EP 2 274 030 B1. These devices comprise a last dose mechanism preventing setting of a dose which exceeds the amount of medicament remaining in the cartridge. Replacing a cartridge allows resetting of this last dose mechanism by pushing the piston rod in a direction opposite to the dispensing direction.

The device described in EP 2 274 030 B1 comprises a housing, a cartridge holder releasably attached to the housing, a piston rod engaging a housing insert and a drive member, a dose setting member guided within the housing to allow rotation of the dose setting member during dose setting and dose dispensing, a clutch for rotationally coupling the drive member and the dose setting member, and a locking element which is rotationally constrained to the housing and is axially movable relative to the housing between a proximal dose setting position and a distal resetting position. The last dose mechanism of this device comprises a sleeve with an opening engaging an enlarged portion in the proximal region of the piston rod if a dose is set which exceeds the amount of medicament remaining in the cartridge. Thus, pushing back the piston rod simultaneously resets the last dose mechanism. This resetting procedure of only pushing back the piston rod is, however, not suitable for devices where the last dose mechanism is not triggered by the axial position of the piston rod.

Last dose mechanisms, like the one in the device described above comprise nuts driven by the rotation of the drive sleeve. However, they do all require that the relative timing of the axial position of the piston rod and the rotational position of the drive sleeve is maintained, i.e. they require that both the axial position of the piston rod and the rotational position of the drive sleeve (relative to the last dose nut) are reset together. Certain aspects of the present disclosure provide an improved resettable drug delivery device in which the last dose mechanism may be reset with fewer constraints, e.g. independent from the axial position of the piston rod.

According to the disclosure, the locking element is axially movable relative to the housing from its proximal dose setting position, in which the locking element is rotationally constrained to the drive member, into a distal dose dispensing position, wherein the locking element is rotationally de-coupled from the drive member, when the locking element is in its distal dose dispensing position or in its distal resetting position. It is one of the main aspects of the present disclosure to provide a locking element which is capable of determining a dose setting mode, a dose dispensing mode and a resetting mode of the device by assuming a respective axial position.

Certain aspects of the present disclosure especially useful in devices in which a relative rotation of the drive member is used for a last dose mechanism, because the locking element allows such a relative rotation of the drive member during dose setting and resetting while preventing undesired movement of the drive member during dose dispensing. The relative rotation of the drive member may be a relative rotation with respect to the housing. Preferably, it is a relative rotation with respect to the dose setting member or to a clutch member which may be rotationally constrained to the dose setting member at least during dose setting and dose dispensing. For example, a last dose nut may be provided interposed between the drive member and the clutch or dose setting member such that a relative rotation of the drive member and the clutch or dose setting member causes the last dose nut to travel axially until it reaches a last dose stop. In a preferred embodiment, the last dose nut is in threaded engagement with one of the drive member and the clutch or dose setting member, preferably the drive member, and rotationally constrained but axially movable relative to the other of the drive member and the clutch or dose setting member, preferably the clutch or dose setting member.

If the drug delivery device preferably comprises a last dose protection mechanism for preventing the setting of a dose, which exceeds the amount of liquid left in a cartridge, this has the advantage that the user knows how much will be delivered before starting the dose delivery. It also ensures that dose delivery stops in a controlled manner without the bung entering the neck portion of the cartridge where the diameter is smaller which may result in an underdose. For example, if the last dose protection mechanism comprises a nut member interposed between the drive member and any other component which rotates during dose setting and dose dispensing, the nut member only moves axially during dose setting and remains stationary with respect to this component during dose dispensing. The nut member may be a full nut or a part thereof, e.g. a half nut.

Preferably, the dose dispensing position of the locking element and its resetting position are different distal positions relative to the housing. The different positions allow coupling and/or de-coupling of one or more further clutches depending on the locking element being in its resetting position or in its dispensing position. For example, the clutch between the drive member and the dose setting member may be coupled in the dose setting and dose dispensing positions of the locking element but de-coupled in the resetting position.

If the device has no dial extension, i.e. has a constant length irrespective of the size of the dose set, handling may be more user-friendly. In addition, this may make the device more reliable by preventing ingression of dirt or the like. For a device without dial extension, the dose setting member and/or the drive member may be axially constrained to the housing.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

Preferably, the housing insert is rotationally constrained to the housing and is axially movable relative to the housing between a (e.g. proximal) dose setting position and a (e.g. distal) resetting position. The piston rod may be in permanent threaded engagement with the housing insert. For example, the housing insert may comprise an inner thread engaging an outer thread of the piston rod, while the drive member is rotationally constrained to the piston rod.

A trigger spring may be interposed between the locking element and the housing insert to push the locking element into its dose setting position. The locking element may be shifted from this dose setting position into a resetting position, e.g. by detaching the cartridge holder, or a dispensing position, e.g. by pushing a trigger or button.

In a preferred embodiment the device further comprises at least one reset spring interposed between the housing and the housing insert. If the cartridge holder is detached from the housing, the reset spring may push the housing insert and the locking element into the resetting position. Preferably, the housing insert is coupled to the locking element such that a distal movement of the housing insert causes a distal movement of the locking element. This may be achieved by a clip engagement allowing relative axial movement in one direction but preventing relative axial movement in the opposite direction. In other words, although the housing insert entrains the locking element as the cartridge holder is detached from the housing, the locking element is free to move axially with respect to the housing insert if the cartridge holder is attached to the housing.

Preferably the device further comprises a button provided at the proximal end of the housing. The locking element may be axially constrained to the button. Thus, the locking element is moved axially upon actuation of the button, i.e. upon axial movement of the button. Coupling the button to the locking element may further be beneficial if the axial movement into the resetting position of the locking element is used to entrain the button to couple or de-couple a clutch, for example the clutch between the dose setting member and the drive member. The locking element may be coupled to the clutch, e.g. via the button, such that the clutch is axially moved relative to the housing when the locking element is moved from its proximal dose setting position to its distal resetting position, which rotationally de-couples the dose setting member and the drive member.

A clutch spring, e.g. interposed between the dose setting member and the clutch, may be used to maintain the rotationally coupled condition between the drive member and the dose setting member if the button or trigger is not activated nor is the device in the resetting mode. Especially in spring driven devices this clutch may be used to withstand the force or torque exerted by the drive spring between dose setting and dose dispensing or in an at rest condition.

In a further development of this embodiment, the clutch between the dose setting member and the drive member is a slipping clutch with first clutch teeth on the drive member and second clutch teeth on a clutch sleeve, which is rotationally constrained to the dose setting member during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the bias of the clutch spring by allowing the sleeve and/or the clutch element to translate axially against the force of the clutch spring. This may result in an oscillating axial movement of the sleeve and/or the clutch element due to continued disengagement and following re-engagement into the next detented position. An audible click may be generated by this re-engagement, and tactile feedback may be given by the change in torque input required.

Preferably, the clutch between the drive member and the dose setting member is a slipping clutch which allows relative rotation between the drive member and the dose setting member in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

In another preferred embodiment, the drug delivery device further comprises a gauge element radially interposed between the outer housing and the dose setting element. The gauge element is axially movable relative to the outer housing and in threaded engagement with the dose setting element. The outer housing may comprise at least one aperture and the gauge element may comprise at least one aperture. If the dose setting element is a number sleeve which comprises markings on its outer surface, at least one of the markings is visible through the aperture in the gauge element and the aperture in the outer housing during dose setting and dose dispensing. The term aperture may include a simple opening the outer housing or gauge element or a transparent window or lens. A window in the outer housing may be incorporated using a 'twin-shot' moulding technology. For example, the outer housing is moulded during a 'first shot' in a translucent material, and the outer cover of the outer housing is moulded during a 'second shot' in an opaque material.

The gauge element may be axially guided within the outer housing such that rotation of the dose setting element causes an axial displacement of the gauge element. The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the outer housing. The gauge element may have the form of a shield or strip extending in the longitudinal direction of the device. As an alternative, the gauge element may be a sleeve. In an embodiment of the disclosure, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow view only on a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the outer housing and relative to the outer housing. In other words, the dose setting element does not perform a translational movement during dose setting. This prevents that the dose setting element is wound out of the outer housing or that the outer housing has to be prolonged for covering the dose setting element within the outer housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The injection device may comprise at least one clicker mechanism for generating a tactile and/or audible feedback. A feedback may be generated during dose setting (increasing and/or decreasing a dose), dose dispensing and/or at the end of dose dispensing.

According to a preferred embodiment of the disclosure, a dose is set by rotating a dial grip located at the proximal end of the housing. Delivery of a dose is initiated by pressing the button and displacing the button axially in the distal direction. Dose delivery continues while the button remains depressed, until the complete set dose has been delivered. The mechanism provides audible, visual and tactile feedback both on the setting and delivery of each dose. Preferably, the mechanism contains a helical drive spring to store energy, which is charged during setting of the dose by the action of the user rotating the dial grip. The spring energy is stored until the mechanism is triggered for dispense at which point the energy stored is used to deliver the medicament from the cartridge to the user. Preferably, any dose size can be selected between zero and a pre-defined maximum, in increments to suit the medicament and user profile. The mechanism permits cancelling of a dose without any medicament being dispensed by rotation of the dial grip in the opposing direction to when selecting a dose.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments of the disclosure will now be described with reference to the accompanying drawings, in which:

FIG. 2 shows an exploded view of the components of the device of FIG. 1a;

FIG. 5 shows in a sectional view a detail of the device of FIG. 1a;

FIG. 6 shows a detail of the device of FIG. 1a;

FIGS. 7a-c show in sectional views the sequence of resetting the device of FIG. 1a; and FIG. 7d shows a sectional view of a detail of the device of FIG. 1a.

DETAILED DESCRIPTION

Figure 1A:
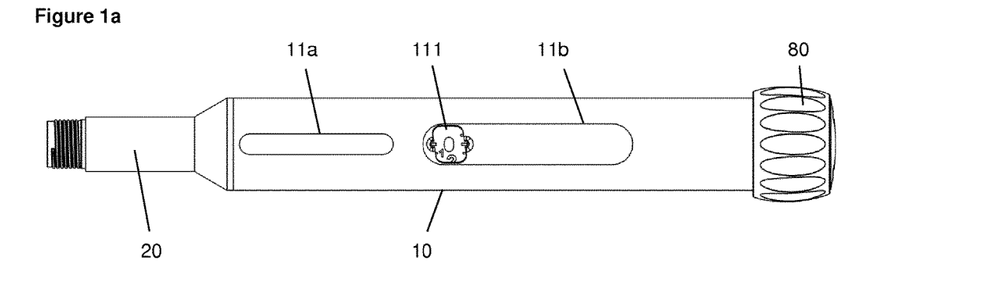
FIG. 1a shows a top view of the drug delivery device of the present disclosure in the minimum dose position.
Figure 2:
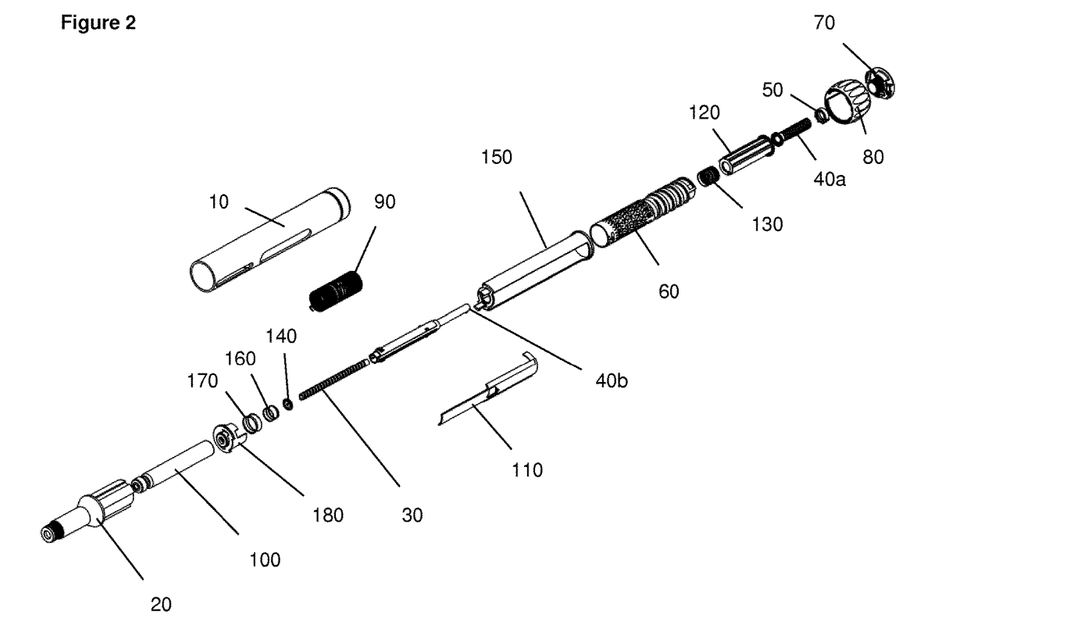
Figure 3A:
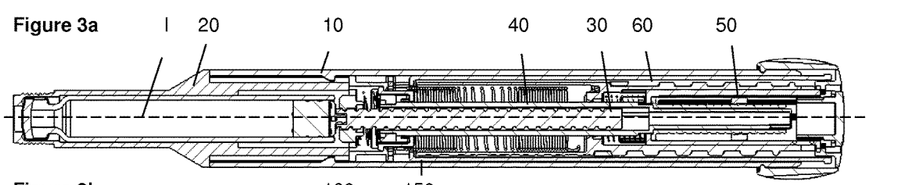
FIGS. 3a, b show sectional views of the device of FIG. 1a in the dose setting mode.
Figure 3B:
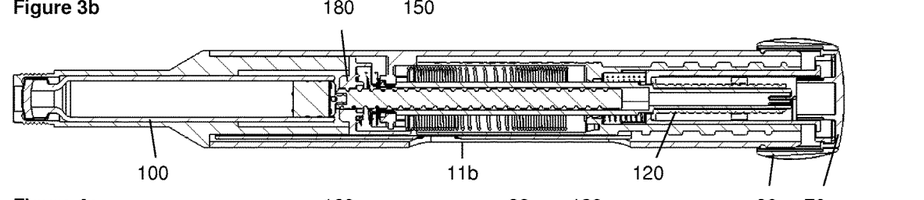
Figure 4A:
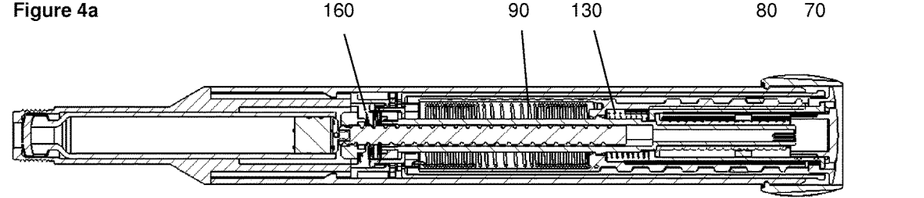
FIGS. 4a, b show sectional views of the device of FIG. 1a in the dose dispensing mode.
Figure 4B:
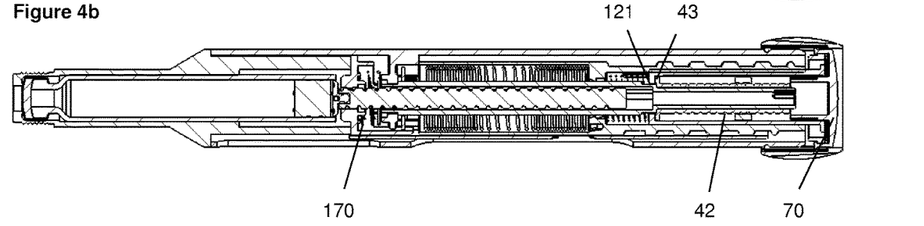
Figure 5:
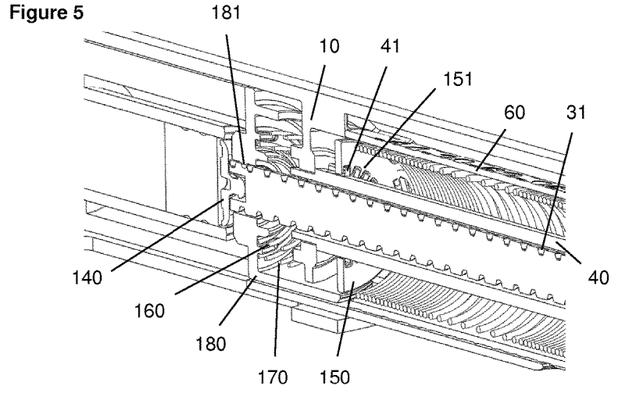
Figure 6:
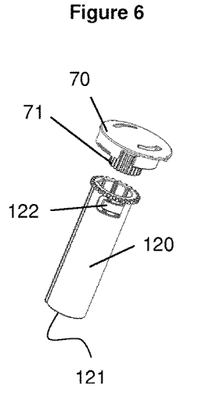

FIG. 1a shows a drug delivery device in the form of an injection pen. The device has a distal end (left end in FIG. 1a) and a proximal end (right end in FIG. 1a). The component parts of the drug delivery device are shown in FIG. 2. The drug delivery device comprises a body or housing 10, a cartridge holder 20, a lead screw (piston rod) 30, a drive sleeve 40, a nut 50, a dose setting element which is a dose indicator (number sleeve) 60, a button 70, a dial grip or dose selector 80, a torsion spring 90, a cartridge 100, a gauge element 110, a clutch element 120, a clutch spring 130, a bearing 140, a locking element 150, a reset spring 160, a trigger spring 170 and a housing insert 180. A needle arrangement (not shown) with a needle hub and a needle cover may be provided as additional components, which can be exchanged as explained above. All components are located concentrically about a common principal axis I of the mechanism which is shown in FIG. 3a.

The housing 10 or body is a generally tubular element. The housing 10 provides location for the liquid medication cartridge 100 and cartridge holder 20, windows 11a, 11b for viewing the dose number on the dose indicator 60 and the gauge element 110, and a feature on its external surface, e.g. a circumferential groove, to axially retain the dose selector 80. The housing 10 further has at least one internal, axially orientated slot or the like for axially guiding the gauge element 110. Further, housing insert 180 is axially guided within housing 10 such that relative rotation is prevented, while, preferably limited, axial relative movement is allowed. In addition, locking element 150 is axially guided in housing 10 such that relative rotation is prevented while axial relative movement is allowed.

The cartridge holder 20 is located at the distal side of housing 10 and attached thereto in a releasable manner, e.g. by a threaded interface. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10. The cartridge holder 20 contains the replaceable cartridge 100. When the cartridge holder 20 is removed, the reset spring 160 forces the housing insert 180, the locking element 150 and button 70 axially in a distal direction, disengaging the clutch 120 and removing the alignment of spline teeth of the clutch 120 to the button 70 thereby allowing the device to be reset.

The piston rod 30 is an elongate lead screw element with an outer thread 31 and at least one axially extending spline or rib. The piston rod 30 is rotationally constrained to the drive sleeve 40 via this splined interface. When rotated, the piston rod 30 is forced to move axially relative to the housing 10, through its threaded interface 31, 181 with the housing insert 180. The bearing 140 is attached to the distal end the piston rod 30, e.g. by a snap connection.

The drive sleeve 40 is a tubular member surrounding the piston rod 30 and being at least in parts received within the dose setting member 60. The drive sleeve 40 extends from the interface with the dose setting member 60 (via the clutch 120 and the upper part 40a of drive sleeve 40) down to a splined tooth interface 41, 151 with the locking element 150. This provides rotational constraint to the drive sleeve 40 during dose setting. When the button 70 is pressed, these spline teeth 41, 151 are disengaged allowing the drive sleeve 40 to rotate under the action of the drive spring 90 dispensing the set dose. The drive sleeve has near its distal end a seat for trigger spring 170. A threaded portion 42 engages last dose nut 50. In the embodiment depicted in the Figures, drive sleeve 40 comprises an upper (proximal) part 40a and a lower (distal) part 40b, which are permanently fixed during assembly of the device. The upper part 40a of drive sleeve 40 is rotationally and axially fixed to the lower part 40b of drive sleeve 40. Thus, the two components act functionally as one component, but are two separate components for assembly reasons. As an alternative, the drive sleeve 40 may be a single component part.

The last dose nut 50 is located between the clutch 120 and the upper part 40a of drive sleeve 40. It is rotationally constrained to the clutch 120, via a splined interface. It moves along a helical path relative to the upper part 40a of drive sleeve 40, via the threaded interface 42, when relative rotation occurs between the clutch 120 and the upper part 40a of drive sleeve 40, i.e. during dialing and resetting only.

The dose setting member 60 is a tubular number sleeve which is constrained at its central flange to the drive sleeve 40 and to the housing 10 at its distal end to allow rotation but not axial translation. The dose setting member 60 is marked with a sequence of numbers, which are visible through opening 111 in the gauge element 110 and the slot-like window 11b in the housing 10, to denote the dialed dose of medicament. The dose setting element 60 is provided with a threaded portion engaging gauge element 110. Splines are provided at or near the proximal end of dose setting element 60 for rotationally constraining the clutch 120 to the dose setting element 60.

The button 70 is splined to the dose setting member 60 when in the dialing condition. This spline interface is disconnected when the button 70 is pressed to trigger a dispense. Ratchet features 71 on the button interact with a clicker arm 122 of clutch 120 during dose dispensing.

The dial grip 80 is radially constrained to the housing 10 and rotationally constrained to the button 70.

The drive spring 90 is attached at one end to the locking element 150 and at the other end to the dose setting member 60. The drive spring 90 is pre-wound upon assembly, such that it applies a torque to the dose setting member 60 when the mechanism is at zero units dialed. The action of rotating the dial grip 80, to set a dose, rotates the dose setting member 60 relative to the locking element 150, and charges the drive spring 90.

The gauge element 110 is constrained to prevent rotation but allow translation relative to the housing 10 via a splined interface. The gauge element 110 has helical features on its inner surface which engage with the helical thread cut in the dose setting member 60 such that rotation of the dose setting member 60 causes axial translation of the gauge element 110.

These helical features on the gauge element 110 also create stop abutments against the end of the helical cut in the dose setting member 60 to limit the minimum and maximum dose that can be set.

The clutch 120 is splined to the dose setting member 60. It is also coupled to the upper part 40a of drive sleeve 40 via a ratchet interface 43, 121, which occurs on an axial abutment. The ratchet 43, 121 provides a detented position between the dose setting member 60 and drive sleeve 40 corresponding to each dose increment, and engages different ramped tooth angles during clockwise and anti-clockwise relative rotation.

The clutch spring 130 is axially interposed between the clutch 120 and the dose setting member 60 to provide an axial force to the ratchet 43, 121 and to bias the clutch 120 onto the upper part 40a of drive sleeve 40.

The bearing 140 is axially constrained to the piston rod 30 and acts on the bung within the liquid medicament cartridge 100.

The locking element 150 is a sleeve-like component with longitudinal slots, which is rotationally constrained to the housing 10 and axially constrained to the button 70. Further, it is coupled to the housing insert 180 such that axial movement of the housing insert 180 in the distal direction, which occurs upon detachment of the cartridge holder 20 at the beginning of resetting, entrains the locking element 150 in the distal direction. On the other hand, axial movement of the housing insert 180 in the distal direction at the beginning of dose dispensing does not cause the housing insert 180 to move axially with the locking element 150. For example, the coupling between the locking element 150 and the housing insert 180 may include hooks (FIGS. 7b, 7c) on the locking element 150 engaging a collar or flange of the housing insert 180.

The housing insert 180 is biased in the distal direction by the reset spring 160 which is axially interposed between an inner wall or web of the housing 10 and the housing insert 180.

Figure 7A:
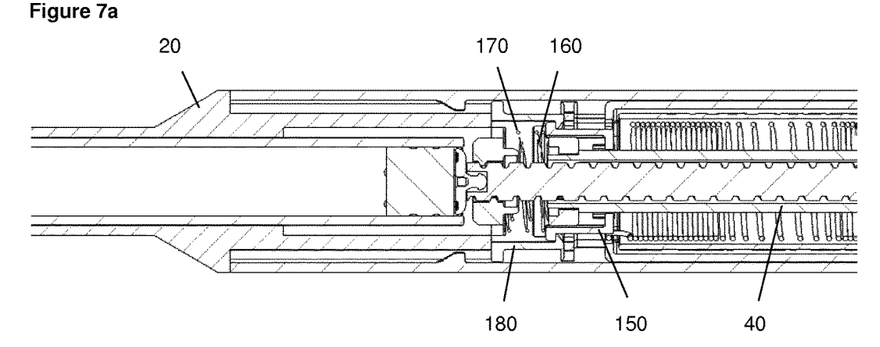
Figure 7B:
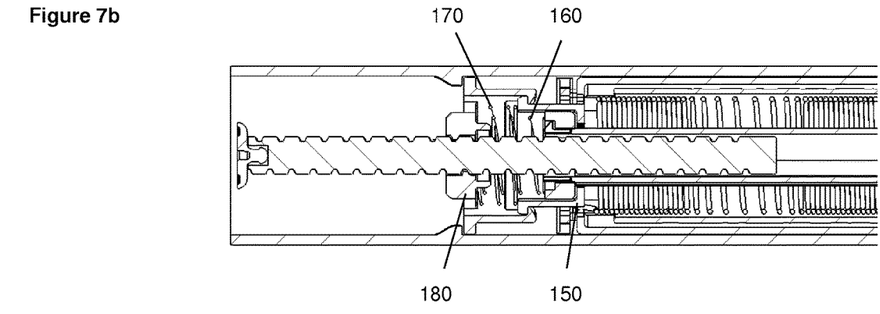
Figure 7C:
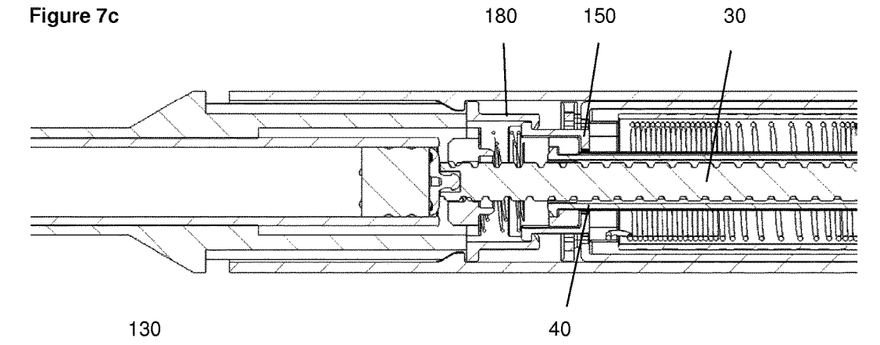

The axial position of the locking element 150 and button 70 is defined by the action of the trigger spring 170, which applies a biasing force on the locking element 150 in the proximal direction. In the at rest position, this ensures that the button 70 splines are engaged with the clutch 120 and that the drive sleeve 40 teeth 41 are engaged with teeth 151 of the locking element 150. FIG. 7a shows that the trigger spring 170 acts between the housing insert 180 and the locking element 150 and the reset spring 160 acts between housing 10 and the housing insert 180. The housing insert 180 is rotationally splined to the housing 10.

With the device in the at rest condition, the dose setting member 60 is positioned against its zero dose abutment with the gauge element 110 and the button 70 is not depressed. Dose marking '0' on the dose setting member 60 is visible through the windows 111, 11b of the housing 10 and gauge element 110 as shown in FIG. 1a. The drive spring 90, which has a number of pre-wound turns applied to it during assembly of the device, applies a torque to the dose setting member 60 and is prevented from rotating by the zero dose abutment between the gauge element 110 and the dose setting member 60.

The user selects a variable dose of liquid medicament by rotating the dial grip 80 clockwise, which generates an identical rotation in the dose setting member 60. Rotation of the dose setting member 60 causes charging of the drive spring 90, increasing the energy stored within it. As the dose setting member 60 rotates, the gauge element 110 translates axially due to its threaded engagement thereby showing the value of the dialed dose. The gauge element 110 has flanges either side of the window area 111 which cover the numbers printed on the dose setting member 60 adjacent to the dialed dose to ensure only the set dose number is made visible to the user.

Figure 1B:
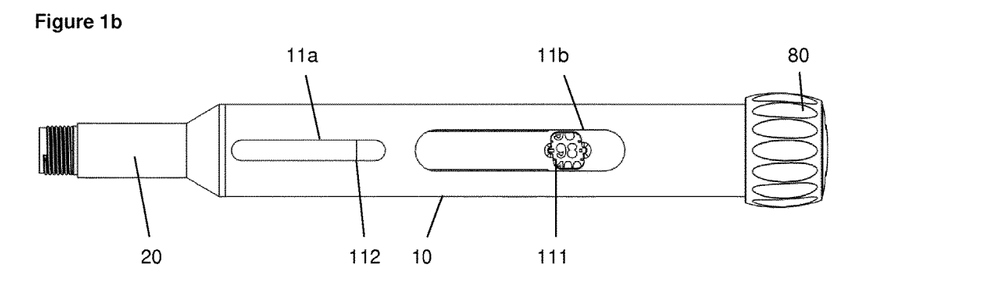
FIG. 1b shows a top view of the drug delivery device of FIG. 1a with a dose of 98 units dialed.

One specific element of this type of mechanism is inclusion of a visual feedback feature in addition to the discrete dose number display typical on devices of this type. The distal end 112 of the gauge element 110 creates a sliding scale (although this could be formed using a separate component engaged with the dose setting member 60 on a different helical track if desired) through a small window 11a in the housing 10. As a dose is set by the user the gauge element 110 translates axially, the distance moved is proportional to the magnitude of the dose set. This feature gives clear feedback to the user regarding the approximate size of the dose set. In FIG. 1a the distal end 112 is at its most distal position and not visible through window 11a. In FIG. 1b the gauge element is in a more proximal position such that the distal end 112 is visible near the proximal end of window 11a. The dispense speed of an auto-injector mechanism may be higher than for a manual injector device, so it may not be possible to read the numerical dose display during dispense. The gauge element 110 feature provides feedback to the user during dispense regarding dispense progress without the need to read the dose number itself. The gauge element 110 display may be formed by an opaque sliding element revealing a contrasting colored component underneath. Alternatively, the concealed component may be printed with coarse dose numbers or other indices to provide more precise resolution. In addition, the gauge element 110 display simulates a syringe action during dose set and dispense.

The drive sleeve 40 is prevented from rotating as the dose is set and the dose setting member 60 rotated due to the engagement of its splined teeth 41 with splined teeth 151 of the locking element 150. Relative rotation must therefore occur between the upper part 40a of drive sleeve 40 and clutch 120 via the ratchet interface 43, 121.

The user torque required to rotate the dial grip 80 is a sum of the torque required to wind up the drive spring 90, and the torque required to overhaul the ratchet feature 43, 121. The clutch spring 130 is designed to provide an axial force to the ratchet feature 43, 121 and to bias the clutch 120 onto the upper part 40a of drive sleeve 40. This axial load acts to maintain the ratchet teeth engagement of the clutch 120 and upper part 40a of drive sleeve 40. The torque required to overhaul the ratchet 43, 121 in the dose set direction is a function of the axial load applied by the clutch spring 130, the clockwise ramp angle of the ratchet 43, 121, the friction coefficient between the mating surfaces and the mean radius of the ratchet features 43, 121.

As the user rotates the dial grip 80 sufficiently to increment the mechanism by 1 increment, the dose setting member 60 rotates relative to the drive sleeve 40 by 1 ratchet tooth 43, 121. At this point the ratchet teeth re-engage into the next detented position. An audible click is generated by the ratchet re-engagement, and tactile feedback is given by the change in torque input required.

Relative rotation of the dose setting member 60 and the drive sleeve 40 also causes the last dose nut 50 to travel along its threaded path, towards its last dose abutment on the upper part 40a of drive sleeve 40.

With no user torque applied to the dial grip 80, the dose setting member 60 is now prevented from rotating back due to the torque applied by the drive spring 90, solely by the ratchet engagement between the upper part 40a of drive sleeve 40 and the clutch 120. The torque necessary to overhaul the ratchet in the anti-clockwise direction is a function of the axial load applied by the clutch spring 130, the anti-clockwise ramp angle of the ratchet 43, 121, the friction coefficient between the mating surfaces and the mean radius of the ratchet features 43, 121. The torque necessary to overhaul the ratchet 43, 121 must be greater than the torque applied to the dose setting member 60 (and hence clutch 120) by the drive spring 90. The ratchet ramp angle is therefore increased in the anti-clockwise direction to ensure this is the case whilst ensuring the dial-up torque is as low as possible.

The user may now choose to increase the selected dose by continuing to rotate the dial grip 80 in the clockwise direction. The process of overhauling the ratchet interfaces 43, 121 between the dose setting member 60 and drive sleeve 40 is repeated for each dose increment. Additional energy is stored within the drive spring 90 for each dose increment and audible and tactile feedback is provided for each increment dialed by the re-engagement of the ratchet teeth 43, 121. The torque required to rotate the dial grip 80 increases as the torque required to wind up the drive spring 90 increases. The torque required to overhaul the ratchet in the anti-clockwise direction must therefore be greater than the torque applied to the dose setting member 60 by the drive spring 90 when the maximum dose has been reached.

If the user continues to increase the selected dose until the maximum dose limit is reached, the dose setting member 60 engages with its maximum dose abutment on the gauge element 110. This prevents further rotation of the dose setting member 60, clutch 120 and dial grip 80.

Depending on how many increments have already been delivered by the mechanism, during selection of a dose, the last dose nut 50 may contact its last dose abutment with the upper part 40a of drive sleeve 40. The abutment prevents further relative rotation between the dose setting member 60 and the drive sleeve 40, and therefore limits the dose that can be selected. The position of the last dose nut 50 is determined by the total number of relative rotations between the dose setting member 60 and drive sleeve 40, which have occurred each time the user sets a dose.

With the mechanism in a state in which a dose has been selected, the user is able to deselect any number of increments from this dose. Deselecting a dose is achieved by the user rotating the dial grip 80 anti-clockwise. The torque applied to the dial grip 80 by the user is sufficient, when combined with the torque applied by the drive spring 90, to overhaul the ratchet 43, 121 between the drive sleeve 40 and clutch 120 in the anti-clockwise direction. When the ratchet 43, 121 is overhauled, anti-clockwise rotation occurs in the dose setting member 60 (via the clutch 120), which returns the dose setting member 60 towards the zero dose position, and unwinds the drive spring 90. The relative rotation between the dose setting member 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially.

When the button 70 is depressed, splines between the button 70 and clutch 120 are disengaged, rotationally disconnecting the button 70 and dial grip 80 from the delivery mechanism. Splines on the dial grip 80 also engage with splines on the housing 10 (so that the dial grip 80 and button 70 do not rotate during dispense). The button 70 acts on the locking element 150 which travels axially and disconnects the splined engagement 41, 151 with the drive sleeve 40. The drive sleeve 40 can now rotate and is driven by the drive spring 90 via the dose setting member 60, and clutch 120. Rotation of the drive sleeve 40 causes the piston rod 30 to rotate due to their splined engagement, and the piston rod 30 then advances due to its threaded engagement 31, 181 to the housing insert 180. The dose setting member 60 rotation also causes the gauge element 110 to traverse axially back to its zero position whereby the zero dose abutment stops the mechanism.

Tactile feedback during dose dispense is provided via a compliant cantilever clicker arm 122 integrated into the clutch 120. This interfaces radially with ratchet features 71 on the button 70. During dispense, as the dose setting member 60 and hence clutch 120 rotate, the ratchet features 71 engage with the clicker arm 122 to produce an audible click with each dose increment delivered.

Delivery of a dose continues via the mechanical interactions described above while the user continues to depress the button 70. If the user releases the button 70, the trigger spring 170 returns the button 70 to its at rest position via the locking element 150, the drive sleeve 40 and the clutch 120 become rotationally constrained and delivery of a dose is halted.

During delivery of a dose, the drive sleeve 40 and dose setting member 60 rotate together, so that no relative motion in the last dose nut 50 occurs. The last dose nut 50 therefore travels axially on the clutch 120 during dialing only.

Once the delivery of a dose is stopped by the dose setting member 60 returning to the zero dose abutment, the user may release the button 70, which will re-engage the drive sleeve 40 spline teeth 41, 151 with the locking element 150 and the button 70 spline with the clutch 120.

The mechanism is now returned to the at rest condition.

Figure 7D:
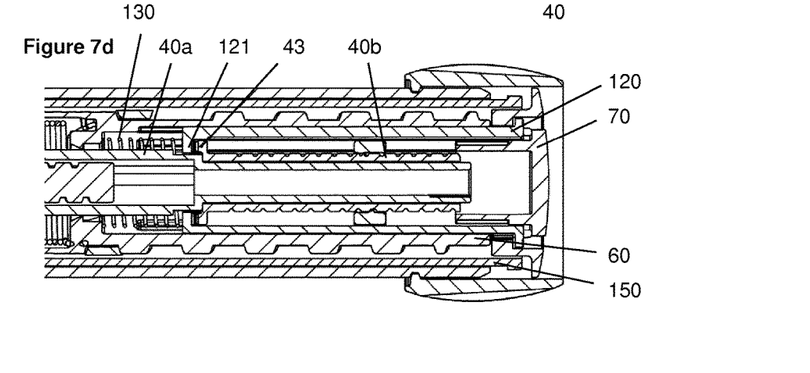

To reset the mechanism, the user first unscrews the cartridge holder 20, which allows the reset spring 160 to move the housing insert 180 in a distal direction. As a result, the housing insert 180 pulls the locking element 150 axially by the same distance. As the locking element 150 and button 70 are linked axially, the button 70 moves axially by the same distance. As the button 70 travels axially the clutch 120 teeth disengage from the button 70. The button 70 also moves the clutch 120 axially in a distal direction during its motion, causing the clutch 120 ratchet 121 to disengage from the ratchet teeth 43 on the upper part 40a of drive sleeve 40 (FIG. 7d). As a result, the dose setting member 60 and drive sleeve 40 are free to rotate relative to each other.

The user can then fit a new cartridge 100 into the cartridge holder 20, and the bearing 140 and piston rod 30 pushed back into the mechanism. As the piston rod 30 is returned into the mechanism, a rotation in the piston rod 30 is generated due to the thread interface 31, 181 with housing insert 180. This piston rod rotation causes the drive sleeve 40 to rotate due to their spline interface, which acts to backwind the last dose nut 50 towards its start position, which is a proximal position in the embodiment shown in the Figures. Since the clutch 120 mechanism is disengaged, the drive sleeve 40 rotation does not transfer significant torque into the dose setting member 60.

During resetting of the mechanism, the force applied to the bearing 140 is less than the force exerted on the housing insert 180 by the reset spring 160, and therefore the housing insert 180 does not move axially in a proximal direction which would otherwise cause the drive sleeve 40 splines 41, 151 to re-engage, locking the mechanism and preventing further reset. Towards the end of reset, the cartridge holder 20 contacts the housing insert 180, and acts to move the housing insert 180 in a proximal direction, reengaging the locking element 150 with the drive sleeve 40 via splines 41, 151 and the clutch 120 with the button 70. During this final stage of reset, the housing insert 180 and piston rod 30 move proximally without rotation at the same rate as the cartridge 100. Therefore no axial compression is generated in the bung of cartridge 100.

REFERENCE NUMERALS

| | |
|---|---|
| 10 | outer housing |
| 11a | opening (window) |
| 11b | opening (window) |
| 20 | cartridge holder |
| 30 | piston rod (lead screw) |
| 31 | outer thread |
| 40 | drive sleeve |
| 40a | drive sleeve upper |
| 40b | drive sleeve lower |
| 41 | teeth |
| 42 | thread |
| 43 | ratchet teeth |
| 50 | nut |
| 60 | dose setting element |
| 70 | button |
| 71 | ratchet features |
| 80 | dose selector |
| 90 | torsion spring |
| 100 | cartridge |
| 110 | gauge element |
| 111 | opening |
| 112 | distal end |
| 120 | clutch |
| 121 | ratchet teeth |
| 122 | clicker arm |
| 130 | clutch spring |
| 140 | bearing |
| 150 | locking element |
| 151 | teeth |
| 160 | reset spring |
| 170 | trigger spring |
| 180 | housing insert |
| 181 | inner thread |
| 1 | longitudinal axis |

The invention claimed is:

1. A drug delivery device for selecting and dispensing a number of user variable doses of a medicament, the device comprising
a housing having a distal end and a proximal end,
a cartridge holder releasably attached to the distal end of the housing,
a piston rod engaging a housing insert and a drive member,
a dose setting member guided within the housing to allow rotation of the dose setting member during a dose setting operation and a dose dispensing operation,
a clutch configured to rotationally couple the drive member and the dose setting member, and
a locking element rotationally constrained to the housing and axially movable relative to the housing between a dose setting position and a resetting position,
wherein the locking element is axially movable relative to the housing from its dose setting position, in which the locking element is rotationally constrained to the drive member, to a dose dispensing position, wherein the locking element is rotationally de-coupled from the drive member when the locking element is in its dose dispensing position or in its resetting position, and
wherein the locking element is coupled to the clutch such that the clutch is axially moved relative to the housing when the locking element is moved from its dose setting position to its resetting position, which rotationally de-couples the dose setting member and the drive member.

2. The drug delivery device according to claim 1, comprising a last dose mechanism with a nut in threaded engagement with the drive member and rotationally constrained but axially movable relative to the clutch.

3. The drug delivery device according to claim 1, wherein the dose setting member and the drive member are axially constrained to the housing.

4. The drug delivery device according to claim 1 wherein the housing insert is rotationally constrained to the housing and is axially movable relative to the housing between a proximal dose setting position and a distal resetting position.

5. The drug delivery device according to claim 1, comprising at least one trigger spring interposed between the locking element and the housing insert.

6. The drug delivery device according to claim 1, comprising at least one reset spring interposed between the housing and the housing insert.

7. The drug delivery device according to claim 1, wherein the housing insert is coupled to the locking element such that a distal movement of the housing insert causes a distal movement of the locking element.

8. The drug delivery device according to claim 7, comprising a button provided at the proximal end of the housing, wherein the locking element is axially constrained to the button.

9. The drug delivery device according to claim 1, wherein the housing insert comprises an inner thread engaging an outer thread of the piston rod, and wherein the drive member is rotationally constrained to the piston rod.

10. The drug delivery device according to claim 1, comprising at least one clutch spring interposed between the dose setting member and the clutch.

11. The drug delivery device according to claim 1, comprising a drive spring interposed between the housing and the dose setting member.

12. The drug delivery device of claim 11, wherein the drive spring comprises a torsion spring.

13. The drug delivery device according to claim 1, comprising a gauge element radially interposed between the housing and the dose setting member, wherein the gauge element is axially movable relative to the housing and in threaded engagement with the dose setting member.

14. The drug delivery device according to claim 13, wherein the gauge element comprises a minimum dose rotational stop and a maximum dose rotational stop and the dose setting member comprises a minimum dose rotational counter stop and a maximum dose rotational counter stop.

15. The drug delivery device according to claim 1, comprising a cartridge containing a medicament.

16. The drug delivery device of claim 15, where the medicament comprises a pharmaceutically active compound.

17. The drug delivery device of claim 1, wherein the dose setting position is a proximal position and the resetting position is a distal position.

18. A method of operating a drug delivery device, the method comprising:
   rotating a dose selector of the drug delivery device to set a dose, the rotating causing:
      rotating of a setting member in a housing of the drug delivery device relative to a locking element of the drug delivery device and moving an indication of a dose set by the dose selector into view through a window of the housing, the locking element being:
         rotationally constrained to the housing of the drug delivery device and axially movable relative to the housing between a dose setting position and a resetting position,
      axially movable relative to the housing from its dose setting position, in which the locking element is rotationally constrained to a drive member, to a dose dispensing position, wherein the locking element is rotationally de-coupled from the drive member when the locking element is in its dose dispensing position or in its resetting position, and
      coupled to a clutch such that the clutch is axially moved relative to the housing when the locking element is moved from its dose setting position to its resetting position, which rotationally de-couples the dose setting member and the drive member, and
   travel of a last dose nut along a threaded path in a first direction to track the total doses delivered from the drug delivery device, the rotating being caused by a first torque from a user, the torque overcoming a first force winding a drive spring and a second force overhauling a ratchet feature and generating a first tactile feedback to the user indicating an incrementing of the dose;
removing a torque from the dose selector, the removal of the torque preventing the dose setting member from rotating back under a torque applied by the drive spring,
counter rotating the dose selector to decrement the dose, the counter rotating being caused by a second torque from the user in a direction opposite the first torque, and the second torque being greater than the first torque, the counter rotating causing travel of the last dose nut in an opposite direction and a second tactile feedback to the user indicating a decrementing of the dose; and
actuating a trigger mechanism to cause the set dose of a medicament to be expelled from the drug delivery device.

* * * * *

UNITED STATES PATENT AND TRADEMARK OFFICE
CERTIFICATE OF CORRECTION

| | | |
|---|---|---|
| PATENT NO. | : 10,569,026 B2 | Page 1 of 1 |
| APPLICATION NO. | : 15/517822 | |
| DATED | : February 25, 2020 | |
| INVENTOR(S) | : Naceur Rekaya and Paul Richard Draper | |

It is certified that error appears in the above-identified patent and that said Letters Patent is hereby corrected as shown below:

In the Claims

In Column 19, Line 31 (approx.), Claim 18, after "a" insert -- dose --

Signed and Sealed this
Thirteenth Day of October, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39), insulin analogue or derivative

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```